United States Patent [19]

Buese et al.

[11] Patent Number: 4,668,563

[45] Date of Patent: May 26, 1987

[54] CONFORMABLE FIBERGLASS CASTING TAPE

[75] Inventors: George J. Buese, East Brunswick; Hee K. Yoon, North Brunswick, both of N.J.

[73] Assignee: Johnson & Johnson Products, Inc., New Brunswick, N.J.

[21] Appl. No.: 873,648

[22] Filed: Jun. 12, 1986

[51] Int. Cl.[4] .............................................. A61L 15/00
[52] U.S. Cl. .................... 428/230; 428/254; 428/259; 428/902
[58] Field of Search ................ 428/230, 254, 259, 902

[56] References Cited

U.S. PATENT DOCUMENTS 3,256,130  6/1966  Nisbet et al. ...................... 428/254
4,366,814  1/1983  Riedel .............................. 428/230

Primary Examiner—Marion C. McCamish
Attorney, Agent, or Firm—Michael O. Tatlow

[57] ABSTRACT

A conformable casting tape made with a combination of high modulus fibers and an elastomeric extensible fiber. The tape is capable of stretching 40 to 200% in the length direction and has a power of between 40 and 125 grams per inch of width at 30% elongation.

7 Claims, 5 Drawing Figures

BAR 1  BAR 2  BAR 3

BAR 1  BAR 2  BAR 3

BAR 1  BAR 2  BAR 3  BAR 4

CONFORMABLE FIBERGLASS CASTING TAPE

FIELD OF THE INVENTION

The present invention relates to an improved fiberglass casting tape. The casting tapes of the present invention have substantial elasticity in their length direction which results in improved conformability, and thus allows better application of the casting tapes to the patient and the resulting cast better fits or conforms to the patient's limb.

BACKGROUND OF THE INVENTION

Plaster of Paris casts have been in use to immobilize body members or limbs for some time. The plaster of Paris bandages have been supplemented and, to some extent, superseded by synthetic cast tapes or bandages which employ polymeric materials on a substrate. The polymeric materials have been cured by exposure to ultra violet light or contained polymers which would cure when reacted with water. Examples of the ultra violet light cured cast can be found in U.S. Pat. No. 3,881,473. More recently, water-cured or water-reactive polyurethane compositions have been used in forming orthopedic casts and the polyurethane materials have largely supplanted other polymeric synthetic casting materials. The polyurethane casting materials are of the type which are disclosed in U.S. Pat. Nos. 4,376,438 and 4,411,262.

The fibrous substrate used in the synthetic casting materials has become, to a large extent, a fiberglass material. The fiberglass materials offer advantages in terms of strength of the finished cast and various constructions of fiberglass fabrics have been used for the substrates for the synthetic casting tapes. The patents mentioned above disclose the use of different fiberglass materials as the substrate for casting tapes. In addition U.S. Pat. Nos. 3,686,725, 3,787,272 and 3,882,857 disclose specific fiberglass materials, or the treatment of fiberglass materials, to produce fiberglass substrates which are particularly suitable for use in orthopedic casts.

U.S. Pat. No. 4,323,061 discloses a cast substrate made from a combination of glass fibers and a second fiber such as cotton, flax, rayon, wool, acrylic resin, nylon, Teflon or polyester. The purpose of the second fiber in the substrate is to hold the curable resin on the substrate.

U.S. Pat. No. 3,332,416 discloses a plaster of Paris cast bandage with a woven substrate made with a combination of elastic and inelastic fibers.

Although fiberglass has been extensively used as a substrate material in orthopedic casts, with different reactive polymers, all of these casting materials suffer certain disadvantages. One of the major disadvantages is the conformability of the casting tape to the body of the patient. Conformability is the characteristic of the casting tape which has been defined as that property which describes the ability of the bandage or casting tape to adapt to or intimately lay down against the compound curves and protrusions of a body member. Fiberglass casting tapes are generally stiffer than casting tapes made of other fibers, and cast technicians and surgeons have some difficulty conforming the fiberglass casting tapes to the limbs of a patient. For this reason, the originally developed fiberglass casting tapes were used, to a large extent, for secondary casting. A secondary cast is a cast which is applied to a patient approximately seven to ten days after the initial cast has been applied. A primary cast is applied to the patient at the time the broken bone in the limb is set. Because of the greater conformability of plaster of Paris cast bandages, plaster of Paris has been employed as a primary casting material. Usually, when the secondary cast is applied, the casting material of choice would be a synthetic cast because of its lighter weight and ability to resist moisture, as compared to plaster of Paris. Also, the conformability is not as critical in a secondary cast as it is in a primary cast. Although the more recently introduced fiberglass casting tapes have greater conformability than the original fiberglass casting tapes, these tapes are still not as conformable as plaster of Paris bandages.

SUMMARY OF THE PRESENT INVENTION

The present invention provides an orthopedic casting tape made of fiberglass which provides greatly improved conformability compared to the prior art fiberglass casting tapes. The casting tape of the present invention uses a knitted substrate which combines fiberglass with an elastic fiber in the substrate. The substrate of the present invention maintains the advantage of the strength of fiberglass and the presence of the elastic fiber provides greater lengthwise extensibility to the substrate which results in a more conformable casting tape. Generally, the conformability of the present tape is significantly improved because the tape has significantly better stretch and return properties than prior art synthetic casting tape and can be readily applied to the patient's limb. The stretch and return characteristics of the present casting tape causes the tape to better conform to the patient. The effect is similar to the ability of elastic garments to conform to the body.

DETAILED DESCRIPTION OF THE INVENTION

Figure 1:
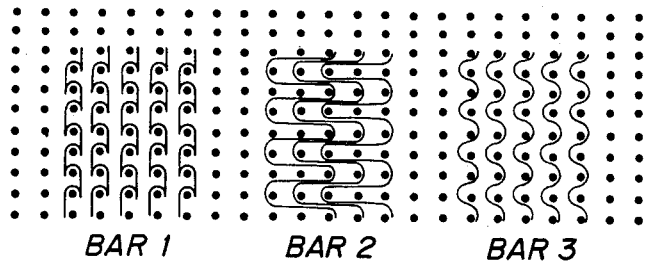
FIGS. 1 and 2 are three bar Raschel knits in which bar 1 performs a simple chain stitch and bars 2 and 3 perform lapping motions to lay in yarn.

The substrate of the casting tape of the present invention is knitted with a combination of continuous filament fiberglass or other high tenacity yarns and elastic filaments or yarns. Fiberglass substrates are generally characterized as made from filaments which are formed into yarn, sized and knitted into the desired structure. In the present invention the substrates are knitted on a Raschel Warp Knitting Machine having 6 to 28 needles per inch. The cast substrate fabrics of the present invention are knitted fabrics which combine a high modulus fiber such as fiberglass, polyaramide, or polyethylene with an elastomeric highly extensible fiber. The high modulus fiber has a modulus of elasticity of $8 \times 10^6$ psi or greater. The elastomeric extensible fiber may be natural rubber or a synthetic elastomer such as polyisoprene, polybutadiene, copolymers of a diene and styrene, copolymers of acrylonitrile and a diene or polychloroprene, copolymers of chloroprene and other monomers, ethylene propylene elastomers including ethylene propylene copolymers and ethylene propylene diene terpolymers, and thermoplastic elastomers which are block copolymers of styrene and butadiene or isoprene. The elastomeric extensible fiber may also be a spandex (polyurethane) fiber. The most common commercially available elastic yarns are natural rubber and spandex. Natural rubber is the preferred elastic yarns in the substrate of the present invention.

The extensible fiber is present in the knit fabric in the warp or wale fibers, i.e., machine direction, but not in the fill fibers. About 0.25 to 25% of the fibers based on the total volume of fibers in the fabric are extensible. The knitted fabric should have a stretch in the length direction of at least 40% and up to 200%. The fabric knitted with elastic yarns has considerable extensibility in the length direction and it is this lengthwise extensibility that provides greater conformability of the resulting casting tape. The extensibility of the fabric of the present invention is at least 40%, and may be as high as 200%, under a static load of 680 grams per inch of width. This is the extensibility of the fabric coated with the prepolymer. The preferred range of extensibility is between 60 and 100%.

Knitted fiberglass fabrics previously employed as substrates in casting tapes had some stretchability or extensibility but would not immediately return or recover to their original length after stretching. The present substrate will return substantially to its original length because of the elastomeric fibers in the substrate. The force returning the substrate to its original length causes the substrate to conform to the patients body.

The elastic fiber component of the substrate can be a wrapped or unwrapped filament. The filament may be wrapped with cotton, nylon or polyester fiber. The elastic filament may be an extruded filament or it may be a cut thread or filament, i.e., the thread or filament may be cut from a sheet of the elastic material. The particular wrapping fiber, if any, is not significant to the present invention. The substrate contains between 75 and 99.75% by volume, of fiberglass or other high tenacity yarn and between 0.25 and 25% by volume of the elastic yarn. The substrate preferably contains between 1 and 6% by volume of the elastic yarn. The stretch characteristics of the fabrics can be controlled by the selection of the type of yarn, the number of elastic filaments and the size or gauge of the filaments as well as the tension on the elastic filaments during knitting and the knitting pattern of the fabric.

The elastic yarn provides significant stretch or elasticity of the fabric in the length direction. A typical prior art fiberglass cast substrate has stretch in the length direction of from about 5 to 35%. As stated above, the cast substrates of the present invention have a stretch greater than 40% and up to 200% and a preferred stretch of between 60 and 100%. The substrates will also have some stretch in the cross direction which is the result of the knit pattern structure rather than the presence of the elastic yarns. The cross direction stretch is between about 30 and 80%.

The fabric of the present invention has relatively low power. Power is the force necessary to stretch a fabric a given percentage. It is expressed as force per unit width, e.g. grams/inch width for a specific elongation. The power should be low to prevent constriction of the patient's limb after the tape is applied to the patient and before the prepolymer cures. After the prepolymer is cured, the power of the fabric is not a consideration as the cured polymer will prevent any further constriction. The power of the fabric of the present invention is preferably between 40 and 175 grams per inch width to stretch the fabric 30%. The power of any particular knit fabric construction may be adjusted by changing the thickness or gauge of the elastic yarn. The power may also be adjusted by changing the number of elastic yarns in the fabric or changing the knit construction and by changing the tension on the elastic yarns during knitting.

The particular elastic thread employed must be compatible with the water curable polyurethane prepolymer employed in the casting tape. Generally, natural and synthetic rubber may be compounded with chemicals which may cause the polyurethane prepolymer to prematurely gel and harden on storage. Such chemicals would include amines, alkali salts, alkaline earth metal salts and active hydrogen containing compounds. If the rubber threads contain an amine compound, it is likely that the polyurethane prepolymer may prematurely cure on storage of the casting tape. Polyurethane, i.e., Spandex, filaments may be used as the elastic filaments in the present invention. However, the polyurethane prepolymer may eventually swell the polyurethane filaments and the filaments will loss their elasticity. The swelling of the polyurethane filaments can be controlled to some extent by cross-linking or coating the filaments. The polyurethane filaments used in the present substrate are those which will retain their elasticity for about one year which is sufficient shelf life in some circumstances. The elasticity of certain types of Spandex filaments are rapidly affected by the polyurethane prepolymer. These filaments lose their elasticity rapidly upon contact with the water-hardenable prepolymer used to coat the substrate.

A simple screening test may be employed to determine if the elastomeric thread will be compatible with a particular polyurethane prepolymer formulation. A mixture of one part by weight of the elastomeric thread is mixed with three parts by weight of the prepolymer formulation and placed in a tube and sealed. The tube is placed in an oven at 70° C. and held for seven days. If the prepolymer is still fluid and the thread is still elastic at the end of the seven-day period, it can be expected that the thread will be compatible with the prepolymer and stable on storage for about one year.

Commercially available rubber threads may also be treated to remove, neutralize or deactivate ingredients which are not compatible with the polyurethane prepolymer. Various extraction processes may be employed. The rubber thread may be extracted with a solvent such as toluene, chloroform, acetone or methylene chloride. The solvent would then be removed by drying. The rubber thread may also be treated with hydrochloric acid. Other acids, such as sulfuric acid, nitric acid, phosphoric acid and organic acids may also be used. The rubber thread is then rinsed with water and then dried. The acid treatment appears to deactivate those rubber chemicals in the threads which cause premature gelation of the prepolymer. The acid or solvent treatment may be performed on the thread before knitting or may be performed on the knitted substrate. A formulation for a natural rubber thread of the type which could be used, after treatment, in the present invention is the following:

|  | Parts |
| --- | --- |
| Crepe Rubber | 100.0 |
| Stearic Acid | 1.0 |
| TiO$_2$ | 10.0 |
| Silica | 10.0 |
| ZnO | 5.0 |
| Sulfur | 2.0 |
| U.V. Stabilizer | 0.2 |
| Accelerator I* | 2.0 |
| Accelerator II* | 1.0 |

(*Typical chemicals are ALTAX, CAPTAX, TUADS, etc.)

The knit patterns that may be used in the manufacture of the substrates of the present invention are numerous. Generally, the fabrics are knitted using at least three bars on the knitting machine, one bar for the elastic thread and two bars for the fiberglass. It is possible to use two bar knit fabrics to produce highly conformable cast substrates for cast applications where high cast strength is not required. Casting tapes to be used for infants are such an application where high strength is not required but highly conformable casting tapes are desirable. In the knitted substrates of the present invention the elastic yarn must give the fabric stretch in the length direction of the fabric. The elastic yarn may be the chain stitch bar 1 in a Raschel knit construction or in bar 2, bar 3 or possibly bar 4 of a 4 bar fabric. If the elastic yarn is in the chain stitch, the second bar would lay in a fiberglass yarn which would extend transversely across the fabric.

The third bar, and the fourth bar if used, could be either fiberglass or another type yarn and could be laid in a zig-zag or a sinusoidal pattern which would increase the crush strength of the final cast by comparison to transversely laid in yarns in these positions. If the elastic yarn is in the chain stitch, tension of the yarn during the knitting will not as strongly effect the stretch characteristics of the fabric as the chain stitch has some extensibility. The elastic yarn will give the chain stitch more extensibility. If the elastic yarn is in bar 2, or bar 3 in 3-bar knit or in bars 2, 3 and/or 4 in a 4-bar knit, the tension in the elastic yarn becomes important. The tension in the elastic yarn should be high enough to cause the fabric to gather or bunch to some moderate degree when it is released from the knitting machine. When the fabric is stretched, the gathers are pulled out and the further extensibility of the fabric is limited by the fiberglass in the chain stitch. The preferred fabric is a 3 bar knit with the elastic yarn in bar 3.

Typical bar patterns for the knit fabric substrates of the present invention are shown in the drawings.

FIG. 1 is a three bar pattern with the elastic thread on bar 3 and fiberglass on bars 1 and 2.

Figure 2:
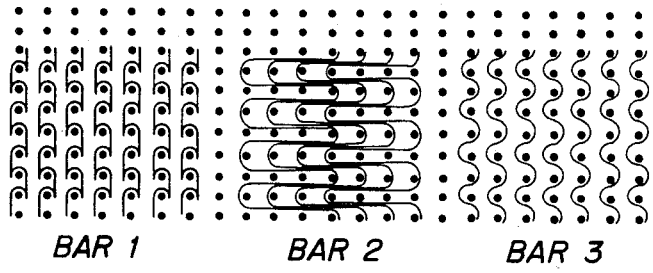

FIG. 2 is a three bar pattern in which the elastic thread is on bar 3 and fiberglass is on bars 1 and 2. This fabric would be heavier than the fabric of FIG. 1 as more fiberglass would be added to the fabric by bar 2.

Figure 3:
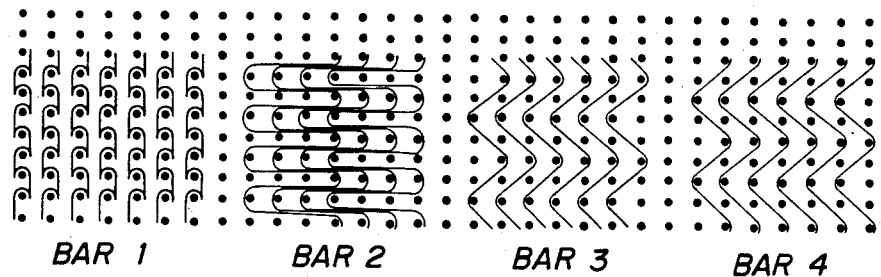
FIG. 3 is a four bar Raschel knit in which bar 1 performs a simple chain stitch and bars 2, 3 and 4 perform lapping motions to lay in yarn.

FIG. 3 is a four bar pattern in which the elastic thread is on bar 1. Bars 2–4 carry fiberglass yarns.

It should be understood that the above bar patterns may be modified. For example, the pattern of FIG. 3 may be employed with an elastic thread in bars 3 and 4 and fiberglass yarn in bars 1 and 2.

Also, the patterns of FIGS. 1 and 2 could be modified by employing a zig-zag pattern on bar 3 similar to that shown in bar 3 or bar 4 of FIG. 3. The particular knit pattern is not important as long as the fabric has the desired power, lengthwise extensibility and volume of fiberglass in the fabric to produce the desired cast strength.

The conformability of casting tapes cannot be objectively measured. However, subjective evaluations of the conformability of synthetic casting tapes based on selective properties have been found to be useful and have good reproductibility between different trained testers. This procedure is explained on page 234 of the proceedings of the 10th Annual Meeting of the Society for Biomaterials, April 27–May 1, 1984. This procedure with some modifications, can be used to compare the conformability of the present casting tapes. The modifications of the procedure are necessary because of the increased conformability of the casting tapes of the present invention and the fact that the present casting tapes exhibit a property, i.e., the ability of the tape to return or the power of the tape which is not found to the same extent in prior casting tapes. To illustrate the conformability of the present casting tape, short arm casts were made with the tape of the present invention, Tape B, and a commercially available fiberglass casting tape A. The results were as shown below:

| Observation Point | Conformability Bandage Property | A | B |
| --- | --- | --- | --- |
| 1 - Upper Forearm | Drape | 10 | 10 |
| 2 - Mid Forearm | M.D. Stretch | 10 | 15 |
| 3 - Mid Forearm | Tack | 5 | 5 |
| 4 - Lower Forearm | Necking | 10 | 14 |
| 5 - Heel of Palm | M.D. Stretch | 10 | 16 |
| 6 - Heel of Palm | Power | 5 | 7 |
| 7 - Back of Hand | Necking | 8 | 14 |
| 8 - Inside of Hand | Twist | 2 | 2 |
| 9 - Bottom of Hand | Fold | 7 | 7 |
| 10 - Bottom of Hand | C.D. Stretch | 10 | 10 |
| 11 - Lower Forearm | C.D. Stretch | 11 | 8 |
| 12 - Lower Forearm | Power | 5 | 7 |
| 13 - Wrist | Mould | 7 | 12 |
|  |  | 100 | 127 |

Figure 5:
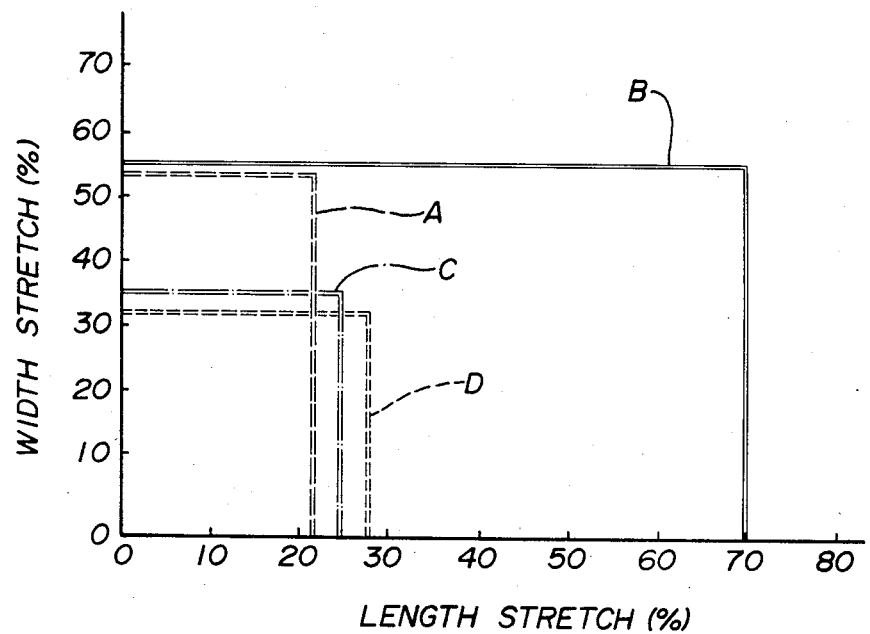
FIG. 5 is a graph comparing the stretch characteristics of the present substrate with the substrates in commercially available casting tapes.

The conformability of the present casting tape compared to the conformability of a commercially available polyurethane based fiberglass casting tapes is shown in FIG. 5. The greater the total amount of stretch, i.e., both length and width, the greater the conformability of the tape. The length stretch is determined by suspending a weight of 680 grams per inch of material width from a 6 inch length of tape and measuring the percent of stretch. The same procedure is repeated to determine the percent stretch in the width direction with the material hung from a side rather than its end. In the figure, line A is an Improved DELTA-LITE Casting Tape; line B is the casting tape of the present invention; line C is K-Cast Casting Tape and line D is SCOTCHCAST 2 Casting Tape. The tape of line B shows a significantly greater degree of stretch in the length direction than the other casting tapes.

Figure 4:
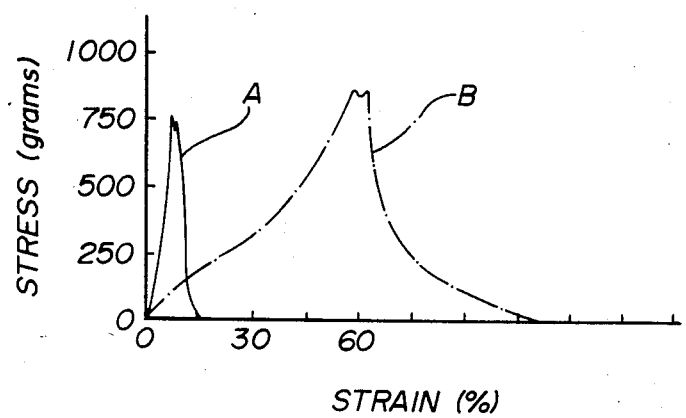
FIG. 4 is a stress strain and recovery curve of the substrate of the present invention and also a curve for a commercially available casting tape substrate.

FIG. 4 illustrates the stretch and return characteristic of the 4.5 inch width of the casting tape of the present invention and a commercially available casting tape four inches wide. The curves in FIG. 4 were generated on an INSTRON Tensile Testing Machine. The curve A is the Improved DELTA-LITE Casting Tape and curve B is the casting tape of the present invention. The samples of fabric were stretched by a force of about 750 grams and then allowed to recover. The downward sloping portion of the curve is the recovery and could be illustrated as returning to the zero point. The curves shown in FIG. 4 are the curves as plotted by the test machine in which the chart paper moves in one direction. The curves show the greater stretch of the substrate fabric of the present invention and the return properties of the fabric. The fabric of the present invention returns faster and also returns to its original length.

The following Examples 1, 2 and 3 show particular substrates that are useful in the present invention.

EXAMPLE 1

A fabric was knitted on an 18-gauge Raschel knitting machine using a 4-bar configuration shown in FIG. 3. The first bar contained a nylon wrapped Spandex yarn, 70 denier, LYCRA T-127 wrapped with two wraps of a 40 denier nylon. There were 41 ends on the first bar. Bar 2 contained DE75 1/0 fiberglass yarn with 38 ends. Bar 3 contained two DE75 1/0 fiberglass yarns for a total of 76 ends, and bar 4 was identical to bar 3. The chain link number for the 6.5 course per inch, $4\frac{1}{2}$ inch fabric were the following:

Bar 1—2, 0, 0, 2;
Bar 2—0, 0, 8, 8;
Bar 3—4, 4, 2, 2 and 0, 0, 2, 2;
Bar 4—2, 2, 4, 4 and 2, 2, 0, 0.

The fabric had a weight of 409 grams per sguare meter (relaxed) and had an elongation of 150%. The power of the fabric was 250 grams at 30% elongation.

EXAMPLE 2

A fabric was knitted on a 24 gauge Raschel knitting machine using a 3-bar pattern of the type shown in FIG. 2. Bars 1 and 2 contained a DE75 1/0 fiberglass yarn and bar 3 contained an unwrapped 90 gauge natural rubber yarn which was sold under the designation L-83 by J. P. Stevens. The first bar had 55 ends, the second bar had 52 ends, and the third bar had 55 ends. The chain link numbers were:

Bar 1—2, 0, 0, 2;
Bar 2—0, 0, 8, 8;
Bar 3—0, 0, 2, 2.

The fabric had a width of $4\frac{1}{4}$ inches and contained 11.94 courses per inch when the fabric was stretched. The fabric had a weight of 461 grams per square meter (relaxed) and 115.0% elongation, and a power of 325 grams at 30% elongation.

EXAMPLE 3

A fabric was knitted on a 24 gauge Raschel knitting machine using a 3-bar configuration of FIG. 1. Bars 1 and 2 contained DE75 1/0 fiberglass yarns and bar 3 contained plain, unwrapped 90 gauge natural rubber yarn. The natural rubber yarn was available from J. P. Stevens under the designation L83. The first and third bars had 49 ends and the second bar had 47 ends. The chain link numbers were:

Bar 1—2, 0, 0, 2;
Bar 2—0, 0, 6, 6;
Bar 3—0, 0, 2, 2.

This $4\frac{1}{4}$ inch width fabric had 11.94 courses per inch when stretched and had a weight of 304 grams per square meter and an elongation of 70%. The power of the fabric was 375 grams at 30% elongation.

The following Examples, 4-7, illustrate the effect of the pretreatment of the yarns with solvents or acids to remove chemical compounds in the yarns which may prematurely gel the prepolymer used to cover the substrate. Generally, a product that will not gel in seven days is equivalent in the finished product to a shelf life of at least one year. One year is a reasonable shelf life for products of this type.

EXAMPLE 4

Approximately 10 grams of untreated 90 gauge rubber yarn (L83 from J. P. Stevens) was placed in a polypropylene tube containing 30 grams of a polyurethane prepolymer of the type disclosed in Example II of U.S. Pat. No. 4,433,680.

The tube was sealed and held at 70° C. in an oven. The prepolymer was hard and had gelled within 3 days. The rubber that was removed from the prepolymer maintained its elasticity. This yarn appears as Number 1 on Table I. The example indicates that this untreated rubber yarn may not be suitable in the practice of the present invention.

EXAMPLE 5

One hundred and seventy yards of 55 end, 90 gauge rubber yarn tape having the designation L83 and manufactured by J. P. Stevens were layered in the bottom of a stainless steel mesh basket. The basket was placed in a large, stainless steel pot. Approximately 12 gallons of toluene was added to the pot so as not to disturb the rubber excessively. At 24 hour intervals, the basket containing the rubber was taken out of the pot and the toluene was replaced with new toluene. The basket was then returned to the pot for an additional 24 hours. This cycle was repeated three times so that the rubber had been exposed to four different extractions by the toluene. The rubber was then taken out and dried to remove the toluene. Approximately 10 grams of the dried rubber were placed in a polypropylene tube containing 30 grams of a polyurethane prepolymer of Example 4. The tube was aged at 70° C. in an oven. After seven days the prepolymer had not became hard and gelled. The polymer hardened on the eighth day.

EXAMPLE 6

One hundred twenty-four yards of 40 end 110 gauge extruded rubber yarn tape, manufactured by the Globe Manufacturing Company under the designation GM32N, was placed on the bottom of a 4000 ml Pyrex beaker. Three thousand milliliters of two normal hydrochloric acid which had been heated to 80° to 85° C. was added to the beaker. The beaker was placed on a hot plate and maintained at a temperature between 70° and 74° C. for $\frac{3}{4}$ hour. The acid was then poured off and the yarn was transferred to a stainless steel mesh basket and thoroughly washed in continuous-flowing water for approximately 1 hour and 20 minutes. After the washing cycle, the rubber was placed over coated steel rods spaced 3 feet apart and dried for approximately five hours. After further drying under a vacuum, about 10 grams of the dried rubber was placed in a polypropylene tube containing 30 grams of the polyurethane-prepolymer of Example 4. The tube was sealed and aged at 70° C. in an oven. The gel time of the prepolymer was determined to be approximately 26 days. The rubber yarn was still elastic.

EXAMPLE 7

A series of rubbers of various gauges were subjected to treatments with hydrochloric acid and also treated with water as a control. The treatment cycles and the gel times are shown in Table I. In all cases, gel times were determined by taking 10 grams of the rubber and adding it to a polypropylene tube containing 30 grams of the prepolymer as in Example 4. The tubes were placed in an oven at 70° C. and the gel times were determined. As previously indicated, a gel time of 7 days or greater is satisfactory for the purposes of the present invention. An additional control was the sample containing only the prepolymer to indicate that the prepolymer would not gel by itself in the indicated time.

TABLE I

| # | Rubber | Gauge | Treatment | Acid Concentration | Temp. | Time | Gel Time (days) |
|---|--------|-------|-----------|--------------------|-------|------|-----------------|
| 1 | L83 | 90 | None | None | None | None | 3 |
| 2 | GM32N | 90 | None | None | None | None | 1 |
| 3 | Qualitex | 110 | None | None | None | None | 1 |
| 4 | L83 | 90 | HCl | 1N | 70° C. | 30 min. | 11 |
| 5 | GM32N | 110 | HCl | 1N | 70° C. | 45 min. | 7 |
| 6 | Qualitex | 110 | HCl | 1N | 70° C. | 45 min. | 18 |
| 7 | Qualitex | 95 | HCl | 3N | 70° C. | 30 min. | 30+ |
| 8 | GM32N | 110 | HCl | 2N | 70° C. | 45 min. | 26+ |
| 9 | GM686 | 90 | HCl | 1N | 70° C. | 45 min. | 7 |
| 10 | GM32N | 110 | Water | — | 100° C. | 1 Hr. | 1 |
| 11 | Qualitex | 110 | HCl | 6N | 75° C. | 45 min. | 21 |
| 12 | Qualitex | 90 | HCl | 4N | 75° C. | 6 Hr. | 19 |
| 13 | L83 | 90 | HCl | 1N | 20° C. | 25 Hr. | 6 |
| 14 | Prepolymer Only | — | — | — | — | — | 35 |

EXAMPLE 8

Casting tape was made using the fabric shown in Example 1. The elastic yarn was a LYCRA T-127. The polyurethane prepolymer described in Example 4 was coated on the fabric at a coating weight of 46% based on the weight of the coated fabric. The fabric weighed 409 grams per square meter and had an elongation of 150%. The bandage was dipped in water to activate the prepolymer and the crush strength of the polymer was determined as follows. Test cylinders were made by wrapping five layers of 4½ inch wide casting tape around a 2¾ inch diameter metal dowel. The cylinders were aged 15 minutes, 1 hour and for 24 hours and their crush strengths were determined. The crush strength of test cylinder samples is determined with a Chatillon compression tester. The samples are compressed a distance of 1 centimeter and the load necessary to deflect the test cylinders determined. Preferably, the crush strength should be greater than 90 pounds for a test cylinders aged 24 hours and made with 5 layers of a 4 inch wide casting tape on a dowel of this size. The particular casting tape employed in this test maintained its conformability and its properties for up to 12 months. The particular sample employed in this test had been aged for 2 months at room temperature. The results of the crush test were as follows:

|  | 15 min. | 1 hr. | 24 hrs. | Set time |
|---|---------|-------|---------|----------|
| Crush strength | 42 lbs. | 58 lbs | 102 lbs | 3.7 min. |

EXAMPLE 9

A 95 gauge extruded natural rubber yarn tape furnished under the designation Qualitex was treated by the process described in Example 6 with 3N HCl for ¾ hours to neutralize ingredients that would react with the polyurethane prepolymer. The treated rubber yarn was incorporated into a 3¼ inch wide Raschel knit fabric employing the pattern described in Example 3. The fabric had a weight of 341 grams per square meter and an elongation of 70%. The fabric was coated with the prepolymer of the type described in Example 4, at a coating weight of 290 grams per square meter, i.e., a coating weight of 46%. Samples of the casting tapes that were aged at 70° C. for 11 days retained their elastic properties. Other samples were aged for twenty-four hours at 70° C. and were tested for crush strength using the procedure set forth in Example 8. The results were as follows:

|  | 24 hrs. | Set time |
|---|---------|----------|
| Crush strength | 95 lbs | 3.0 min. |

We claim:

1. An orthopaedic casting tape containing a fibrous substrate impregnated with a water-reactive polyurethane prepolymer, said substrate comprising a combination of a high modulus fiber and an elastomeric fiber which is not substantially reactive with the prepolymer and which will maintain its elastic properties for at least 12 months after impregnation with the prepolymer, the elastomeric fiber being incorporated in the substrate in the length direction of the substrate to give the substrate an extensibility of between 40% and 200% in the length direction, said substrate having a power such that the force necessary to extend the substrate to 30% elongation is between 40 and 175 grams per inch of substrate width.

2. The casting tape of claim 1 in which the high modulus fiber comprises 99.75–75% by volume of the fiber in the substrate and the elastomeric fiber comprises 0.25 to 25% by volume of the fibers in the substrate.

3. The casting tape of claim 1 in which the substrate has an extensibility in the length direction of between 60 and 100% under a static load of 640 grams per inch of width.

4. The casting tape of claim 1 in which the substrate is a Raschel knit fabric and in which the elastomeric fiber is in the chain stitch of the fabric.

5. The casting tape of claim 1 in which the high modulus fiber is fiberglass.

6. The casting tape of claim 1 in which the elastomeric fiber is natural rubber.

7. The casting tape of claim 1 in which the substrate is a 3 bar Raschel knit fabric and the elastomeric fiber is in bar 3 of the substrate.

* * * * *